United States Patent [19]

Suzuki et al.

[11] 4,435,830
[45] Mar. 6, 1984

[54] X-RAY APPARATUS

[75] Inventors: Hirotsugu Suzuki, Ootawara; Sigeru Urata; Kanichi Okabe, both of Nasu, all of Japan

[73] Assignee: Tokyo Shibaura Denki Kabushiki Kaisha, Japan

[21] Appl. No.: 323,499

[22] Filed: Nov. 20, 1981

[30] Foreign Application Priority Data

Nov. 21, 1980 [JP] Japan .................. 55-164325

[51] Int. Cl.³ ............................... A61B 6/02
[52] U.S. Cl. ...................... 378/197; 378/190
[58] Field of Search ............ 378/181, 197, 190

[56] References Cited

U.S. PATENT DOCUMENTS

| | | | |
|---|---|---|---|
| 2,492,339 | 12/1949 | Wagner | 378/197 |
| 3,281,598 | 10/1966 | Hollstein | |
| 3,784,837 | 5/1972 | Holmstroem | |
| 4,024,401 | 5/1977 | Bernstein et al. | |
| 4,150,297 | 4/1979 | Borggren | |

*Primary Examiner*—Alfred E. Smith
*Assistant Examiner*—T. N. Grigsby
*Attorney, Agent, or Firm*—Schwartz, Jeffery, Schwaab, Mack, Blumenthal & Koch

[57] ABSTRACT

Disclosed is an X-ray apparatus having an X-ray source, an X-ray imaging device in confronting relation to the X-ray source, a first support constructed and arranged for performing generally longitudinal movements for supporting the X-ray source, a second support constructed and arranged for performing generally longitudinal movements for supporting the X-ray imaging device, a first movable base for mounting the first support, a second movable base independent of the first movable base for mounting the second support, and a connector releasably interconnecting the support at a predetermined distance for allowing the support as interconnected to be operated in unison.

15 Claims, 4 Drawing Figures

X-RAY APPARATUS

BACKGROUND OF THE INVENTION

The present invention relates to an X-ray apparatus and more particularly to an improvement of an X-ray apparatus having individual support means for supporting an X-ray source device and an X-ray imaging device for use in making diagnoses of patients' blood circulation systems.

Angiography has been used to gain an increased diagnostic resolution or accuracy in making diagnoses of patients' blood circulation system, such as for heart disease. The human heart comprises four chambers, that is, a right ventricle, a right atrium, a left ventricle, and a left atrium. The heart also has three valves, i.e., an aortic valve, a mitral valve, and a tricuspid valve, and has coronary arteries running around the heart. It is sometimes difficult to make a correct diagnosis of the heart with angiography, since X-ray images picked up in some directions show a superimposed ventricle and spinal cord, or superimposed blood vessels. It has recently become customary for an increased diagnostic resolution to take pictures of a heart in various directions depending on the purpose of the diagnosis in order to avoid making an incorrect diagnosis.

A conventional X-ray apparatus for the diagnosis of blood circulation systems comprises an X-ray tube, an X-ray image detector, for example, an image intensifier, and a C-shaped or U-shaped arm connecting the X-ray tube and the image intensifier integrally with its end portions. The patient lying on an extension of a table is positioned between the X-ray tube and the image intensifier so that the rays generated by the tube are aligned or directed onto him. Since the X-ray tube and the image intensifier are integrally connected, they cannot be used in combination with another installed film changer which is constructed so as to automatically feed the film or with another installed X-ray source device.

In other conventional X-ray apparatus, an X-ray tube support and an image intensifier support are comprised of telescoping sections adapted for vertical extension and contraction. These are mounted on the crane for movement in horizontal directions. When it has been necessary to pick up an X-ray image in a desired direction with this system, it has been time-consuming to position the X-ray tube and the image intensifier in central alignment with each other, since the holders are independently constructed. When a positioning exposure lamp in a movable X-ray aperture device has been used to determined an X-ray exposure zone, it has been required to move the table and the patient or the examinee on the table so as to be clear of such exposure until the positioning is completed. When the examinee and the table are in a position for taking pictures, the exposure lamp in the movable aperture device cannot be used, and hence it has been necessary to let the X-ray tube and image intensifier face each other as the operator thinks fit and cause an X-ray to penetrate the body of the examinee for ascertaining whether a desired part of the body is displayed on a monitor screen before its picture is taken. When the zone of exposure to radiation from the X-ray tube is shifted out of the area to be exposed, the operator is subjected to an X-ray exposure which is quite dangerous. Combined use of independently separate devices as described above results in an impaired ease with which such devices are operated, causing diagnostic resolution to be lowered.

SUMMARY OF THE INVENTION

Therefore, it is an object of the present invention to provide a novel and improved X-ray apparatus including support means for an X-ray source means and for an X-ray imaging device which are movable independently.

It is another object of the invention to provide a novel X-ray apparatus which can be used for general diagnosis but which may be used in combination with other installed X-ray sources or other installed imaging devices.

It is a further object of the invention to provide a novel X-ray apparatus in which independent supports for an X-ray source and for an X-ray imaging device are releasably connected with each other to be operated in unison.

It is still another object of the invention to provide a novel X-ray apparatus in which independent supports for an X-ray source and for an X-ray imaging device, respectively, are releasably connected integrally at a predetermined distance for easy positioning to effect alignment with each other.

It is furthermore an object of the invention to provide an X-ray apparatus which reduces the risk of the operator being subjected to an X-ray exposure.

In accomplishing the foregoing objects, there has been provided according to the invention an X-ray apparatus comprising an X-ray source, X-ray imaging device in confronting relation to the X-ray source, a first longitudinally movable support supporting the X-ray source, a second longitudinally movable support supporting the X-ray imaging device, a first movable base mounting the first support, a second movable base independent of the first movable base mounting the second support, and a connector which releasably interconnects the supports at a predetermined distance for allowing the supports to be operated in unison as an interconnected unit. The first base and support and the second base and support, whether coupled or not, are both restrained to movement along the same rectilinear path.

Other objects, features and attendant advantages of the present invention will become readily apparent as the apparatus becomes better understood by reference to the following Detailed Description of Preferred Embodiments, when considered in connection with the accompanying drawings.

BRIEF DESCRIPTION OF THE DRAWINGS

In the drawings, forming a part hereof, in which like reference characters denote like parts in the various views.

DETAILED DESCRIPTION OF PREFERRED EMBODIMENTS

Figure 1:
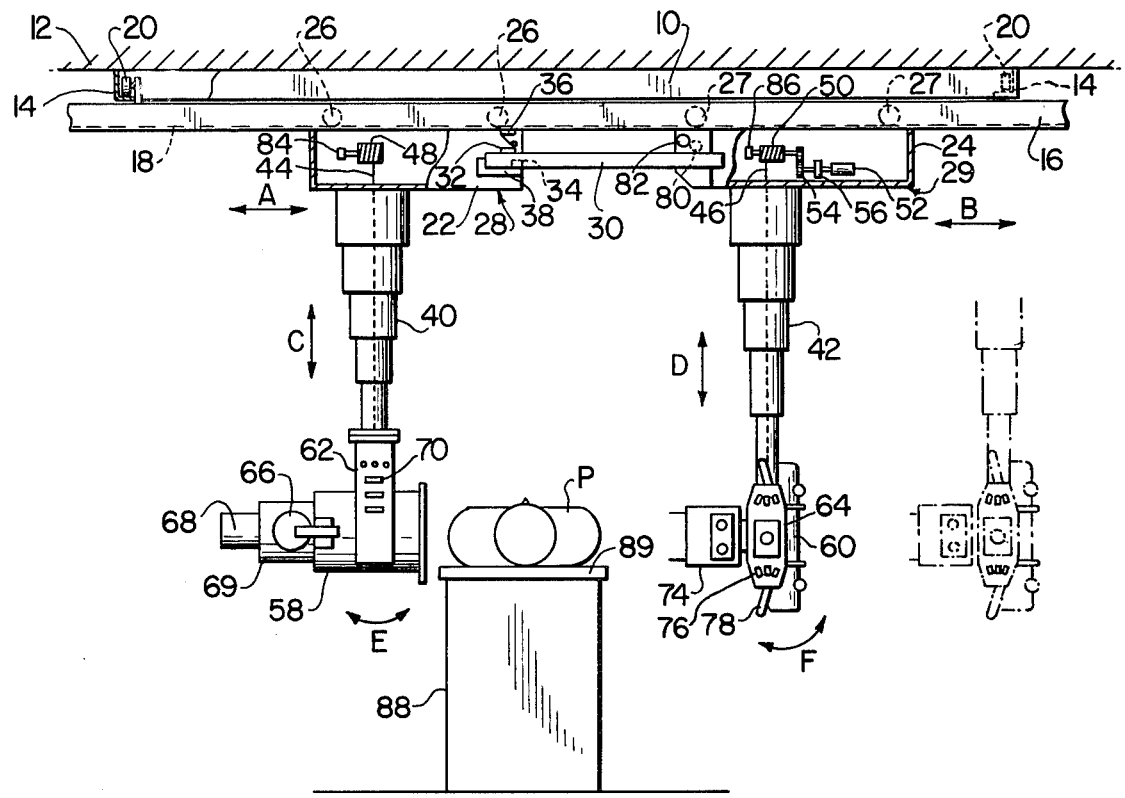
FIG. 1 is a side view showing an X-ray apparatus according to an embodiment of the invention in which, in addition to the solid line illustration, there is also a phanton line illustration showing the X-ray source and support in an additional one of its possible positions.
Figure 2:
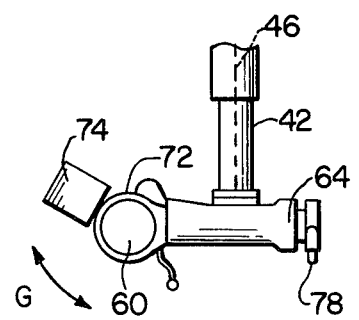
FIG. 2 is a side view of a portion of the apparatus shown in FIG. 1, in which the X-ray source is rotated by 90° about both a vertical and horizontal axis from the position shown in FIG. 1.

Now there will be described a first embodiment of the invention according to FIGS. 1 and 2. In FIG. 1, a guide rail frame 10 is mounted by anchor bolts (not shown) on a ceiling 12, which has a pair of guide rails 14 which are parallel to each other and are perpendicular to the plane of the drawings. A guide rail frame 16 or guide element which has a pair of parallel guide rails 18 (only one shown) is located below and attached to the guide rails 14 of the guide rail frame 10 by wheels 20 mounted on the guide rail frame 16 and extending in a direction transverse to the guide rail frame 10. The guide rail frame 16 is reciprocally movable along the guide rails 14 in a to-and-fro direction or perpendicularly to the plane of the drawing. A pair of mounting bases 22 and 24 have respective sets of wheels 26 and 27 (only one side shown) held in engagement with the guide rails 18 such that the mounting bases 22 and 24 are supported on the guide rails 18 for reciprocable movement therealong in horizontal directions or directions of the arrows A, B, respectively.

The mounting bases 22 and 24 are movable in every direction in the horizontal plane through the guide rail frames 16. Therefore, movable bases 28 and 29 comprise the mounting bases 22 and 24 with wheels 26, 27 and the guide rail frame 16. One of the mounting bases 24 has a connecting arm 30 projecting from the side of the base in the direction against the mounting base 22. Arm 30 has a projecting dog 32 and an electromagnet 34 respectively projecting and mounted adjacent to the distal portion end of the connecting arm 30. The other mounting base 22 has a detector, such as a microswitch 36, attached in coacting relation to the projecting dog 32 of the connecting arm 30, and a clamp in the form of a member 38 of ferromagnetic material on the side of the base to be attached by the electromagnet 34. The connecting arm 30 and clamp in the form of member 38 form a connector for releasably interconnecting the bases 22, 24 together. The length of connecting arm 30, or so-called S.I.D. (Source Image Distance), is properly determined according to the size of subject to be X-rayed, exposure time, capacity of the X-ray tube, etc.

Extensible and contractible supports, such as multi-walled pipes or telescoping sections 40, 42, which telescope vertically or in the directions of the arrows C, D, are respectively mounted on the undersides of the mounting bases 22 and 24. The telescoping sections 40, 42 are telescopically movable by wires 44, 46, respectively, wound around take-up drums 48, 50 with balancing springs (not shown). The balancing may be effected by other balancing systems using counterweights, for example. The telescoping sections 40, which serve as an X-ray imaging device support member, are only manually telescopically movable with the balancing spring; and the telescoping sections 42, which serve as an X-ray source support, are either automatically or manually telescopically movable with the take-up drum connected to a motor 2 through a gear 54 and an electromagnetic clutch 56 mounted on the mounting base 24. The clutch 56 is connectable for automatic operation and disconnectable for manual operation of the telescoping section 42. An imaging device, which may take the form of an image intensifier 58, for example, and an X-ray source, which may take the form of an X-ray tube 60, for example, are mounted on the telescoping sectins 40, 42 at their distal ends by holder members 62, 64, respectively. The telescoping sections 40, 42 and the holder members 62, 64 jointly constitute support members. The holder member 62 supports the image intensifier 58 for angular movement in the direction of the arrow E and secures the image intensifier 58 at a desired angle. Shown in FIG. 1 is a cine recording camera 66, a television camera 68, an optical system 69 for transmitting an output image from the image intensifier 58 to the cine recording camera 66 or the television camera 68, and control switches 70. The control switches 70 operate to change the states of "lock" and "unlock" of the mounting base 22 and support member 40.

The holder member 64 is supported on the telescoping sections 42 for rotation about an axis of the latter in the directions of the arrow F. The X-ray tube 60 is supported on the holder member 64 for rotation in the direction of the arrow G in FIG. 2 by a supporting fork 72 mounted on the holder member 64. These rotatable parts can be secured at desired angular positions. Indicated at 74 is a movable X-ray aperture device mounted at an outlet of the X-ray tube 60, and indicated at 76 is a control switch box with operating handles 78 disposed on the holder member 64. The base 24 supports a motor 80 as a drive means and a wheel 82 driven by the motor 80 through an electromagnetic clutch (not shown). The motor 80 and the clutch are connected with the control switches 70 through a cable (not shown). The wheel 82 is arranged to be in contact with the undersurface of the guide rail 18 so that the mounting base 24 moves reciprocally along the guide rail 18 in the directions of the arrow B.

Position detectors 84, 86, such as potentiometers, are mounted respectively on the take-up drum 48, 50 in the bases 22, 24 for detecting vertical positions of the X-ray image intensifier 58 and X-ray tube 60. The X-ray tube 60 may be automatically controlled by a servomechanism control circuit (not shown) which actuates the motor 52 by the output of the position detectors 84, 86 to bring the X-ray tube 60 into horizontal alignment with the image intensifier 58 or into a position located obliquely with respect to the image intensifier 58.

The table 88 for the patient or examinee P is arranged between the X-ray tube 60 and the image intensifier 58, the patient P lying on the extension 90 of the table 88.

The apparatus thus constructed will operate as follows:

When a control switch 70 on the holder member 62 for the image intensifier 58 is actuated, the motor 80 in the mounting base 24 is energized to drive the moving base 29, namely, the holder member 64 for the X-ray tube 60, from a retracted position shown by the phantom line position in FIG. 1 toward the holder member 62 for the image intensifier 58 in the direction of the arrows B. As the holder members 62, 64 are spaced at a predetermined distance, the connecting arm 30 allows the microswitch 36 to be actuated by the projecting dog 32, whereupon the motor 80 is stopped and at the same time the electromagnet 34 is energized by the microswitch 36 to be attracted to the member 38, allowing the bases 22, 24 to be interconnected at the predetermined interval. When image intensifier 58 is manually moved in the vertical direction, the position detector 84 detects the vertical position of the image intensifier 58 and causes the motor 52 to drive the X-ray tube 60 so as to follow the image intensifier 58 in a verticaL sense in the direction of arrows D. The position detector 86 stops the X-ray tube 60 in a position in which the X-ray tube 60 is held in proper alignment with the image intensifier 58. The holder members 62, 64 can be moved and positioned in unison in the directions of arrows A, B and perpendicularly to the plane of the drawings by operating the switches 70 on the holder member 62 for the image intensifier 58. It will be apparent from the drawing and from the foregoing that, when the holder members 62, 64 and associated supports 40, 42 are moved in unison in the direction of arrows A, B when interconnected by the connecting arm 30, they will all travel in the same direction (i.e., the direction of arrows A, B) with respect to the guide element 16, which direction is the same as that which establishes the predetermined distance by which the supports are spaced apart. Of course, in the embodiment shown, the direction which establishes the predetermined distance is the direction in which the connecting arm 30 extends. Upon disconnection of the bases 22, 24 by releasing the connecting arm 30 by the switches 70, the bases 22, 24, namely, the holder members 62, 64, can be used independently of each other, and the holder member 64 for the X-ray tube 60 can be actuated both manually and automatically by the electromagnetic clutch 56 in the base 24.

With the bases 22, 24, namely, the holders, connected together by the connecting arm 30, they can be positioned in unison and in a position corresponding to that in which the X-ray exposure is directed within the bounds of the image intensifier for easier operation thereof and to prevent the operator from being subjected to an X-ray exposure; and yet the apparatus can be used in a manner similar to that of an apparatus having a conventional C-shaped or U-shaped arm. Furthermore, the decrement and scattering of the X-ray beam can be kept to a minimum. When the holder members 62, 64 are disconnected from each other, they can be used with another installed apparatus. Thus, the apparatus according to the present invention finds a wide variety of applications.

The embodiment described above and shown in the drawings is only by way of illustration.

Figure 3:
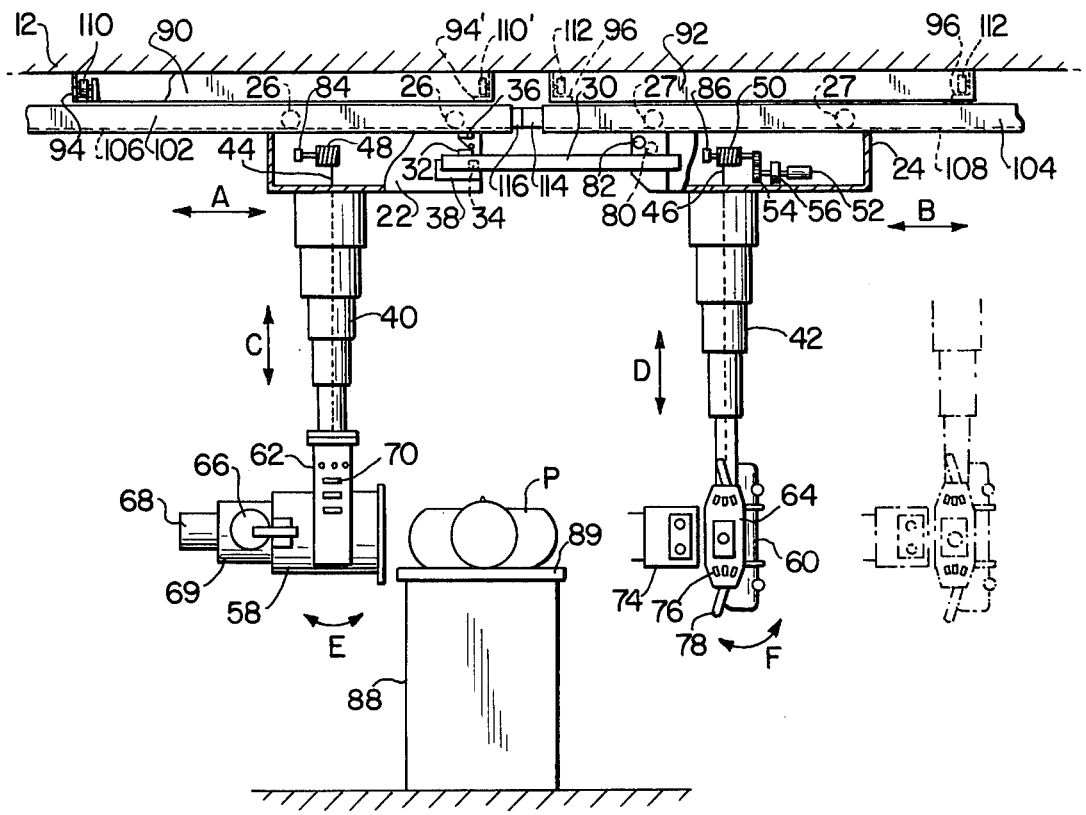
FIG. 3 is a side view showing an X-ray apparatus according to another embodiment of the invention.
Figure 4:
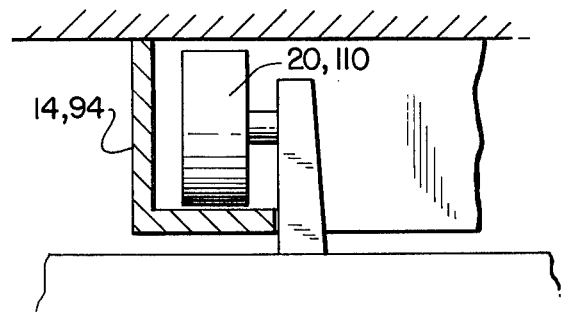
FIG. 4 is an enlarged fragmentary view of the wheel and rail arrangement shown in a smaller scale at the uppermost left of both FIGS. 1 and 3.

For example, while in the illustrated embodiment the holder members 62, 64 for the image intensifier 58 and the X-ray tube 60 are movable on the single guide rail frame 16, the guide rail frame or guide element 16 may be divided into to sections which can be connected and disconnected as desired by an electromagnet as with the connecting arm 30 as shown in FIG. 3.

In FIG. 3, the guide rail frames 90 and 92 are side-by-side and mounted by anchor bolts (not shown) on the ceiling 12, which have a pair of guide rails 94, 94' and 96, 96', respectively. A pair of guide rail frames 102 and 104 have a pair of guide rails 106 and 108, respectively (only one side shown). The guide rail frames 102 and 104 are located below and attached to the guide rails 94, 94' and 96, 96' of the guide rail frames 90 and 92 by wheels 110, 110' and 112, 112' mounted on the guide rails frames 102, 104, respectively. The guide rail frames 102 and 104 are separately and reciprocally movable along the guide rails 94 and 96 in a to-and-fro direction or perpendicularly to the plane of the drawing. The guide rail frames 102 and 104 hold the mounting bases 22 and 24 through their sets of wheels 26 and 28, respectively. One of the guide rail frames, 104 for example, has an electromagnet 114 on its side surface and the other guide rail frame 102 has a member 116 of ferromagnetic material on its corresponding surface. Energization and de-energization of the electromagnet 114 by control switches 70 effects connection and disconnection of the guide rail frame 102 with and from the guide rail frame 104. The electromagnet 114 and magnetic member 116 constitutes coupling between the guide rail frames 102 and 104. When the divided guide rail frames are disconnected, the X-ray tube 60 and the image intensifier 58 can be independently moved in directions perpendicular to the plane of the drawings for a wider variety of modes of operation to take X-ray pictures.

Although the connecting arm 30 and the microswitch 36 have been described as determining and detecting the distance between the holder members 62 and 64, an extensible and contractible electrically-operated piston-cylinder arrangement may be mounted on the mounting base 24 for determining a desired distance between the holders by controlling the degree of projection of the piston from the cylinder.

While in the foregoing embodiment the guide rail frame 10 is attached to the ceiling 12, the guide rail may be mounted on a floor or side wall.

The connecting and moving mechanisms for the X-ray source and X-ray imaging device may be interchanged with each other.

Various other modifications may be made in the present invention without departing from the scope thereof.

What is claimed is:

1. An X-ray apparatus, comprising:
    an X-ray source;
    an X-ray imaging device in confronting relation to said X-ray source;
    a first longitudinally movable support, said X-ray source being coupled with and supported by said first support;
    a second longitudinally movable support, said X-ray imaging device being coupled with and supported by said second support;
    a first movable base on which said first support is mounted;
    a second movable base independent of said first movable base on which said second support is mounted, each of said first and second movable bases having a mounting base for mounting each of said first and second supports, a plurality of wheels and a guide for moving said mounting base by said wheels; and
    a connector releasably interconnecting said supports at a predetermined distance apart for allowing said supports to be operated in unison when interconnected.

2. An X-ray apparatus according to claim 1, wherein said connector comprises a connecting arm which is provided on one of said bases, said connecting arm having a distal end portion remote from said one base, said connector also comprising a clamp which is provided on the other of said bases for clamping the distal end portion of said connecting arm.

3. An X-ray apparatus according to claim 2, wherein said connecting arm includes a projection and a member of magnetic material on its distal end portion and wherein said clamp includes a switch to be operated by said projection and an electromagnetic member for clamping said magnetic material member.

4. An X-ray apparatus according to claim 1, wherein at least one of said first and second movable base includes a drive means for driving said one base in reciprocal movement.

5. An X-ray apparatus according to claim 1, wherein said guide comprises a first guide rail frame having a pair of guide rails and second guide rail frame having a pair of guide rails which are arranged perpendicularly to said first guide rail frame, said guide rails of said second guide rail frame being movable on the guide rails of said first guide rail frame through a plurality of wheels.

6. An X-ray apparatus according to claim 5, wherein said second guide rail frame comprises a pair of guide rail frames which are separately movable on said guide rails of said first guide rail frame through a plurality of wheels on each guide frame of said pair of guide rail frames, each guide rail frame of said pair having one of said mounting bases mounted thereon by the wheels of the mounting base.

7. An X-ray apparatus according to claim 6, wherein said pair of guide rail frames includes a coupling for releasably coupling each other together.

8. An X-ray apparatus according to claim 7, wherein said coupling comprises an electromagnet mounted at one of said pair of guide rail frames and a member of magnetic material mounted at the other of said pair of guide rail frames.

9. An X-ray apparatus according to claim 1, wherein at least one of said first and second supports comprises telescoping sections.

10. An X-ray apparatus according to claim 1, wherein said first support includes a holder for holding said X-ray source for angular movement with respect to said first support.

11. An X-ray apparatus according to claim 10, wherein said holder further comprises a means for rotatably supporting said X-ray tube of said X-ray source.

12. An X-ray apparatus according to claim 1, wherein said second support includes a holder for holding said X-ray imaging device for angular movement with respect to said second support.

13. An X-ray apparatus according to claim 1, wherein said first base and support, on the one hand, and said second base and support, on the other hand, are both restrained for movement along the same rectilinear path.

14. An X-ray apparatus, comprising:
an X-ray source;
an X-ray imaging device in confronting relation to said X-ray source;
a first longitudinally movable support, said X-ray source being coupled with and supported by said first support;
a second longitudinally movable support, said X-ray imaging device being coupled with and supported by said second support;
a first movable base on which said first support is mounted;
a second movable base independent of said first movable base on which said second support is mounted;
a guide, having a guide element, said first and second movable bases engaging said guide element and being movable therealong; and
a connector releasably interconnecting said supports at a predetermined distance apart for allowing said supports to be operated in unison when interconnected,
said guide and said first and second movable bases being mutually so constructed and arranged that, when the supports are interconnected by said connector and operated in unison, said supports will both travel in the same direction with respect to said guide element, which direction is the same as that which establishes the predetermined distance by which the supports are spaced apart.

15. An X-ray apparatus according to claim 14, wherein said guide element is a first guide rail frame and wherein said guide includes a second guide rail frame, the first guide rail frame being movably coupled with the second guide rail frame for movement in a direction with respect to the second guide rail frame which is perpendicular to said direction in which said first and second movably bases will travel in unison with respect to said guide element.

* * * * *